(12) United States Patent
Mordekhay

(10) Patent No.: US 7,118,708 B2
(45) Date of Patent: Oct. 10, 2006

(54) SYSTEM OF SAMPLE MEDIUM CARRIERS WITH BUILT-IN MEMORY ELEMENTS AND INFORMATION INPUT/OUTPUT STATION FOR THE CARRIERS

(75) Inventor: Vladimir Mordekhay, Campbell, CA (US)

(73) Assignee: Automated Biotechnology, Inc.

( * ) Notice: Subject to any disclaimer, the term of this patent is extended or adjusted under 35 U.S.C. 154(b) by 0 days.

(21) Appl. No.: 10/624,399

(22) Filed: Jul. 21, 2003

(65) Prior Publication Data

US 2004/0092025 A1    May 13, 2004

Related U.S. Application Data

(60) Provisional application No. 60/424,760, filed on Nov. 12, 2002.

(51) Int. Cl.
*B01L 9/00*    (2006.01)

(52) U.S. Cl. .................... 422/58; 422/99; 422/102; 422/100; 422/63; 422/68.1

(58) Field of Classification Search ................ 422/58, 422/99, 100, 102, 104, 63, 67, 68.1
See application file for complete search history.

(56) References Cited

U.S. PATENT DOCUMENTS

| | | | |
|---|---|---|---|
| 4,761,075 A * | 8/1988 | Matsushita et al. ........... 356/39 |
| 5,827,479 A * | 10/1998 | Yamazaki et al. ............ 422/67 |
| 6,064,754 A | 5/2000 | Parekh et al. | |
| RE37,485 E | 12/2001 | Vestal | |
| 6,617,146 B1 * | 9/2003 | Naccarato et al. .......... 435/243 |
| 6,637,473 B1 * | 10/2003 | Ganz et al. ................. 141/130 |
| 6,726,820 B1 * | 4/2004 | Frazier ....................... 204/451 |
| 6,730,517 B1 * | 5/2004 | Koster et al. ................ 436/47 |
| 6,890,485 B1 * | 5/2005 | Stylli et al. ................ 422/68.1 |
| 2002/0150450 A1 * | 10/2002 | Bevirt et al. ........... 414/225.01 |
| 2003/0087446 A1 * | 5/2003 | Eggers ....................... 436/48 |
| 2003/0215360 A1 * | 11/2003 | Ruddock ..................... 422/63 |

OTHER PUBLICATIONS

Finnish Company Oy Ideos, Ltd. http://www.ideos.fi/default.asp?toc=2.

* cited by examiner

*Primary Examiner*—Brian R. Gordon

(57) ABSTRACT

The invention relates to a system that consists of a plurality of sample plate carriers with resettable built-in memory devices and an information input/output station for the aforementioned memory devices. In the preferred embodiments, the aforementioned station comprises a storage cassette for the carrier, or an intermediate station through which the sample plate carrier is passed when it is handled by a robot arm. The cassette has an input/output port for selectively entering or extracting information into or from the memory unit. This information may relate to the specific sample plates or sample plate carriers that holds the memory element and may relate to positions of the carriers and events that occurred with the samples on the specific sample plates. Each sample plate carrier is provided with a locking mechanism for removably locking the sample plates in the carrier. The carriers have asymmetric shape for correct orientation of the carriers in the cells of the cassette and are provided with a number of features that facilitates interaction with grippers and actuators of various types for automatic loading/unloading of the sample plate carriers into/from the cassette and for transportation between the working stations.

4 Claims, 15 Drawing Sheets

SYSTEM OF SAMPLE MEDIUM CARRIERS WITH BUILT-IN MEMORY ELEMENTS AND INFORMATION INPUT/OUTPUT STATION FOR THE CARRIERS

CROSS-REFERENCE TO RELATED APPLICATIONS

The subject matter of this patent application is related to that of U.S. Provisional Patent Application No. 60/424,760 filed on Nov. 12, 2002 the full disclosure of which is incorporated herein by reference. The present patent application is also related to pending patent application Ser. No. 10/615,733 filed by the same applicant on Jul. 7, 2003.

FIELD OF THE INVENTION

The present invention relates to the field of chemistry and biochemistry and, in particular, to the analytical methods and apparatuses for loading, unloading and analyzing samples, e.g., by matrix assisted laser desorption ionization (MALDI) technique. More specifically, the invention relates to a system of sample plate carriers with a resettable built-in data chip and a data input/output station for the aforementioned carriers. The invention also relates to a method for high-volume sample array analysis based on the use of the aforementioned sample plate carriers. The invention also relates to a storage cassette for the aforementioned sample plate carriers, samples themselves, as well as to a method of tracing the positions, events, and history of events that occurred with the plate carriers and sample plates.

BACKGROUND OF THE INVENTION

Mass spectrometers have become one of the essential tools of the biochemistry lab. Biochemists take advantage of the capabilities of mass spectrometers to determine molecular weights of biomolecules, monitor bioreactions, detect post-translational modifications, perform protein, and oligo-nucleotide sequencing, and many more applications. During the past decade, one of the methods, which became most successful for the mass spectrometric analysis and investigation of large molecules is a method known as MALDI (Matrix-Assisted Laser Desorption Ionization). This method, which in application to time-of-flight (TOF) mass spectrometry (MS) is known as MALDI-TOF MS, is a relatively novel technique in which a co-precipitate of an UV-light absorbing matrix and a biomolecule is irradiated by a nanosecond laser pulse. The sample (analyte) is suspended or dissolved in a matrix.

Most of the laser energy is absorbed by the matrix, which prevents unwanted fragmentation of the biomolecule. Matrices are small organic compounds that are co-crystallized with the analyte. It seems that the presence of the matrix spares the analyte from degradation, resulting in the detection of intact molecules as large as 1 million Da (Dalton or amu are atomic mass units used in microbiology). For example, in time-of-flight mass spectrometers, the ionized biomolecules are accelerated in an electric field and enter the flight tube. During the flight in this tube, different molecules are separated according to their mass-to-charge ratio and reach the detector at different times. In this way each molecule yields a distinct signal. The method is used for detection and characterization of biomolecules, such as proteins, peptides, oligosaccharides, and oligonucleotides, with molecular masses, e.g., between 200 and 350,000 Da.

Another advantage of MALDI in application to mass spectrometry is that this method allows for vaporization and ionization of non-volatile biological samples from a solid-state phase directly into the gas phase.

The most important step in MALDI is sample preparation. During this step, the matrix and analyte are mixed, and the mixture is dried on a probe or, as it is more common now, on a sample plate. Upon preparation, the sample is loaded into the mass spectrometer.

A laser beam serves as the desorption and ionization source in MALDI. The matrix plays a key role in this technique by absorbing the laser light energy and causing part of the illuminated substrate to vaporize. A rapidly expanding matrix plume carries some of the analyte into the vacuum with it and aids the sample ionization process. The matrix molecules absorb most of the incident laser energy minimizing sample damage and ion fragmentation (i.e., soft ionization). Nitrogen lasers operating at 337 nm (a wavelength that is well absorbed by most UV matrices) are the most common illumination sources because they are inexpensive and offer the ideal combination of power/wavelength/pulsewidth. However, other UV and even IR pulsed lasers have been used with properly selected matrices.

Once the sample molecules are vaporized and ionized, they are transferred into a mass spectrometer where they are separated from the matrix ions and individually detected.

A sample support used in the aforementioned system may comprise a thin, substantially square plate of stainless steel or another suitable material, e.g., approximately 1.5 mm thick and 50 mm wide sample. An example of a sample support geometry is the one described, e.g., in U.S. Reissued Patent RE 37,485 filed by Marvin L. Vestal and published on Dec. 25, 2001. The system is equipped with a support transport mechanism working in vacuum and intended for automatically inputting and outputting each of the sample supports into and from the sample receiving chamber of the mass spectrometer.

The sample plate carrier described in the aforementioned earlier inventions may contain precisely located holes to allow the position and orientation of the plate to be accurately determined relative to a moveable stage, which is required both in the sample loading step and in the ion source of the mass spectrometer. The sample plate also contains a plurality of precisely determinable sample positions on the upper sample-receiving surface of the plate. The sample plate may thus contain 100 sample positions each identified by a sample spot, which is about 2.5 mm in diameter in a precisely known location on the plate, with each sample support being suitable for accepting a few microliters of sample solution.

The sample support is rigidly attached to a ferromagnetic material handle, which is used to engage an electromagnetic device for the purpose of transporting the sample plate between component systems. The sample plate has two or more precisely located holes which locate the sample holder when installed in the sample receiving stage in the ion source of the mass spectrometer and in the sample transport trays.

Another example of a similar sample plate support or holder intended for atmospheric-pressure MALDI can be found in co-pending U.S. patent application Ser. No. 10/615,733 of the same applicant. The sample plate carriers of this application are designed for automatic loading/unloading into and from the sample storage device, such as a sample plate carrier cassette which is used in conjunction with a computer-controlled sample holder handling mechanism for taking a sample plate carrier from the aforementioned cassette, extracting the sample plate from the carrier, inserting the sample plates to the target flange for interface with a mass spectrometer orifice, securing it in a working position for analysis, unloading back to the sample plate carrier after completion of the analysis, and inserting the sample plate to a desired cell of the sample storage device.

In the specific embodiments of aforementioned U.S. patent application Ser. No. 10/615,733, the system is provided with two holder transportation units. The sample holder or carrier of the aforementioned type has specifically shaped slots for engagement with grippers of a mechanism intended for extraction of the sample plate carriers from the cassette and for loading them into the cassette and for disconnection of the sample plates from the respective carriers. Information about individual positions of the holders is stored in the memory of a common central processing unit, which also controls operation of all actuating mechanisms of the aforementioned modules. In other words, the aforementioned carriers only hold the sample plates with multiple sample cells and do not carry any address information or data about the samples or sample plate carriers themselves or about the analysis history, etc.

If analysis is relatively low in volume, it is common that the aforementioned information is loaded manually to a mass spectrometer and to the central processing unit for handling the sample plate carriers. However, when a large number of samples is to be analyzed with the use of automatic loading/unloading devices such as industrial robots or the transportation system of the type described in the aforementioned patent application, it becomes difficult to analyze different samples by different methods, as well as to keep the correct data regarding the sample history and location of various sample plates in the cells of the sample storage device. It is also difficult to keep information on the exact location of the samples on the respective sample plates.

Attempts have been made to solve the above problems by providing the sample holders with a permanent bar code, which may simplify tracking between the sample and the generated data. For example, U.S. Pat. No. 6,064,754 issued on May 16, 2000 to R. Parekh, et al. discloses a computer-assisted methods and apparatus for identification and characterization of biomolecules in a biological sample. It is stated in the aforementioned patent that methods of indexing the information record to the proper sample can include the assignment of matching numbers to the record and the sample. This process is preferably automated through the use of barcodes and a barcode scanner. As each sample is processed, the scanner is used to record the sample identification number into the memory, which tracks the sample through its various manipulations, thus preserving the link between record and sample. The use of barcodes also permits automated archiving and retrieval of stored samples. The barcodes can be engraved on the sample plate carriers permanently.

However, using this approach, it is still possible to misalign data because the sample plate carriers can be reusable and the holders with the same permanent bar codes could be used for carrying different samples for analysis at different time.

In another approach, a removable bar code sticker attached to the sample plate can be used to uniquely identify the plate holder for specific sample plate and for specific type of analysis. However, it may be more difficult to clean such plate holders for reusing. Furthermore, an undesired situation may occur when the bar code sticker is separated from the holder during handling. Another disadvantage is that for reuse of the holder the old sticker has to be removed and replaced by a new one. This requires additional time. Some companies offer labeling machines specially for labeling the microbiological sample plate carriers with barcode stickers. For example, Finnish company Oy Ideos, Ltd. produces state-of-the-art identification and data collection system. When the sample plate carrier with the barcode sticker arrives at the laboratory, all the information associated with the sample is read and automatically entered into the laboratory information system with the use of a special data-reading unit supplied by the aforementioned company. However, the use of automatic barcode reading devices does not solve the problems associated with barcodes in general.

Another disadvantage of the barcoded sample plate carriers is that they are difficult to protect from contamination and cross-contamination during handling by the robotic systems or other mechanical grippers.

The aforementioned Finnish company Oy Ideos, Ltd. also produces manually handled carriers for blood analysis (phlebotomy) samples. All appropriate information is sent to the laboratory by the re-usable sample plate carriers that will replace requests, which normally have been written on paper. The data is written on memory built into an RF ID board. Compared with the traditional technologies (such as barcodes) used for phlebotomy data transfer, the application of the RF ID technology offers such feature as possibility to add and modify data on the fly so that information can be updated at any point of time during the sample handling process.

Although the aforementioned system of manually-handled carriers with a built-in memory is efficient and convenient due to wireless access to the memory of the carrier for reading/wring the information, the carries of the aforementioned type use RF communication and should have relatively large dimensions. They are intended for manual transportation, handling, loading, and unloading into a blood-analysis control system installed in a laboratory. In other words, the phlebotomic sample plate carriers of Oy Ideos, Ltd. are inapplicable for genomic studies, where thousands of samples have to be treated during a short period of time on a series of sequentially arranged units of biomedical analytical equipment. The sample plate carrier with transmission and receiving of RF signals should have large overall dimensions. Furthermore, radio frequency signals generated by the cards may interfere with sensitive instruments of the analytical laboratory, to say nothing of the case if such carries were installed side by side into the cells of the sample plate carrier cassette where it would be impossible to identify the required carrier without activation of all of them at the same time.

Thus, sample plate carriers with on-rout information about the samples and history of processing suitable for high throughput analysis of high-volume samples, such as those required, e.g., for genomic MALDI mass-spectrometric study, are still unknown.

OBJECTS OF THE INVENTION

It is an object of the invention to provide a system that consists of sample plate carriers with built-in memory elements and an input/output station for inputting/outputting data into/from the aforementioned memory elements. It is an object of the invention to provide sample plate carriers with memory elements storing on-rout information about the samples and history of processing suitable for high throughput analysis of high-volume samples. It is another object to provide the aforementioned sample plate carriers suitable for genomic MALDI mass-spectrometric study. It is another object to provide the sample plate carrier of the aforementioned type provided with an electronic nonvolatile re-recordable memory device for recording information on the media that are used for sample deposition, sample modification, sample alternation, or sample analysis. It is another object to provide the sample plate carrier of the aforementioned type provided with a memory device for writing the information on the current steps and results of the analysis. A further object is to provide the aforementioned sample plate carriers that could be compactly packed into cells of a sample storage cassette without mutual interference. Still another object is to provide a sample plate carrier storage cassette with means for individual access to each sample plate carrier through the inlet port of the cassette. An additional object is to provide the aforementioned sample plate carrier, which is universal in that it can interact with various gripping mechanisms for serving units of analytical equipment in the line of analysis. A further object is to provide the aforementioned sample plate carrier that allows replacement of the sample plates of different geometry with rewriting data in accordance with characteristics of new samples. It is object of the invention to provide a sample plate carrier for use without direct contact of mechanical actuators and grippers with the sample plate. Another object is to provide a sample plate carrier that is free of contamination during handling and does not require the use of removable stickers with information. An additional object of the invention is to provide an efficient way for establishing unique correlations between information data, sample plate with a specific samples, and methods of analysis. It is an object to provide the aforementioned sample plate carrier with a reliable lock to prevent a sample plate from accidental disengagement from the carrier. It is another object to provide the aforementioned sample plate carrier, which has a non-symmetrical geometry to insure the unique orientation of the holder in the cassette and other carrier holding devices.

SUMMARY OF THE INVENTION

The invention relates to a system that consists of a plurality of sample plate carriers with resettable built-in memory devices and an information input/output station for the aforementioned memory devices. In the preferred embodiment the aforementioned station comprises a storage cassette for the carriers. The cassette is designed for storing special sample plate carriers for holding sample plates with a plurality of samples intended for analysis, e.g., for AP-MALDI mass spectrometry. Each sample plate carrier is provided with a memory element, such as a miniature nonvolatile information storage device having input/output contacts for interaction with appropriate contacts or terminals provided in each cell of the cassette. The cassette has an input/output port for selectively entering or extracting information into or from the memory unit. This information may relate to the specific sample plates or sample plate carriers that holds the memory element and may relate to positions of the carriers and of the samples on the sample plates and events that occurred with the samples on the specific sample plates. The contacts of each sample plate carrier may also interact with input/output stations of other instruments or storage devices included into the line of analysis. Each sample plate carrier is provided with a locking mechanism for removably locking the sample plates in the carrier. The carriers have asymmetric shape for correct orientation of the carriers in the cells of the cassette and are provided with a number of features that facilitate interaction with grippers and actuators of various types for automatic loading/unloading of the sample plate carriers into/from the cassette and for transportation between the working stations.

DETAILED DESCRIPTION OF THE INVENTION

As has been mentioned above, the invention relates to a system that consists of a plurality of sample plate carriers that carry sample plates with samples and have a built-in memory and an information input/output station for inputting/outputting information relating to the sample plate carriers into/from the aforementioned built-in memory. The elements of the system, i.e., the sample plate carriers and the information input/output station in the form of a carrier storage cassette will be considered separately. The following description will begin from the description of the sample plate carriers.

In the context of the present invention, the term "sample plate" has a broader meaning and covers sample media in different forms, e.g., sample vials, ampoules, rectangular plates, disks and bodied of other regular or irregular shapes capable of carrying liquid or solid samples.

Figure 1A:
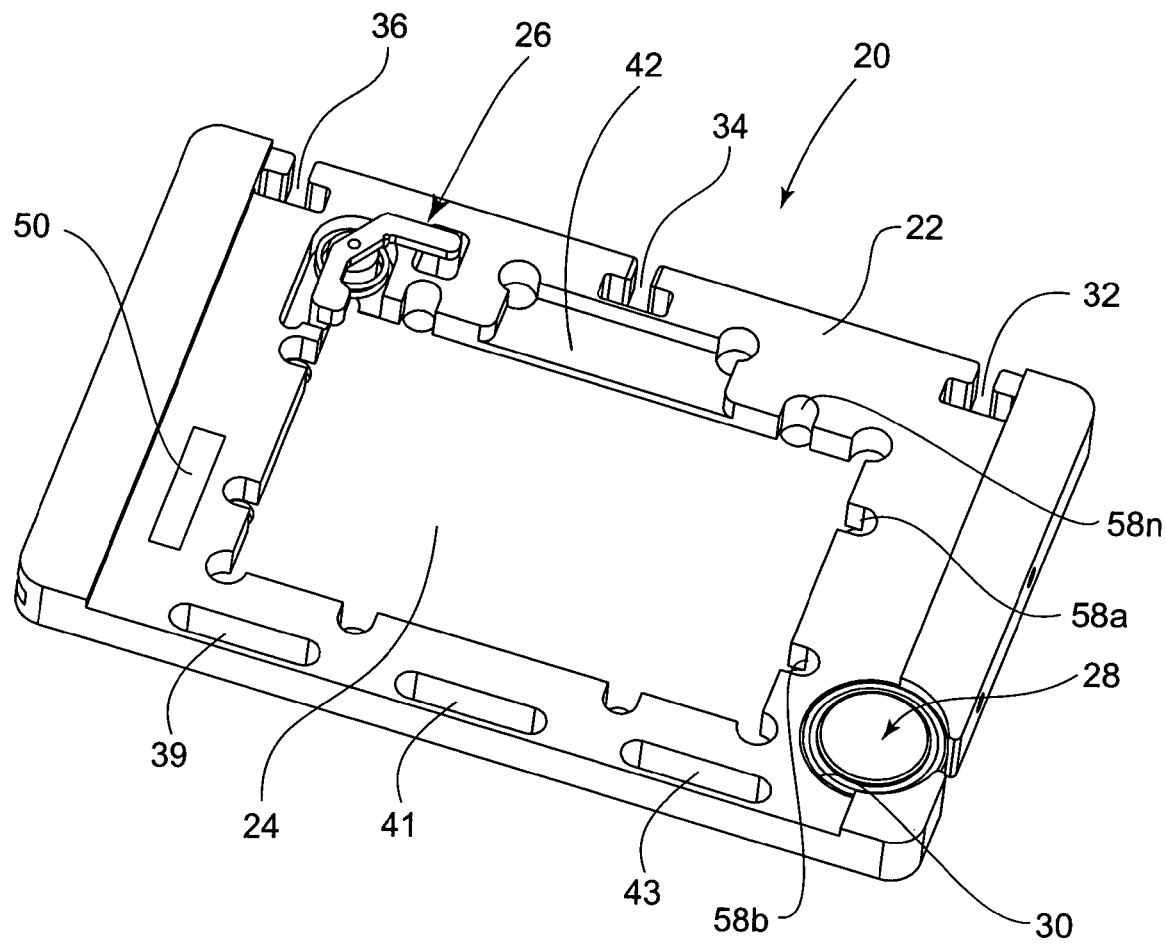
FIG. 1A is a three-dimensional view of a sample plate carrier in accordance with one embodiment of the invention with a sample plate removed for clearness of the drawing.

FIG. 1A is a three-dimensional view of a sample plate carrier in accordance with one embodiment of the invention with a sample plate removed for clearness of the drawing. The sample plate carrier of this embodiment will be first described in general, and specific features of the carrier will be considered in more detail later.

As shown in this drawing, a sample plate holder or carrier 20 for holding, protecting, and carrying sample plates has a carrier body 22 that has a central portion and a peripheral portion. The central portion has a sample plate recess 24 conformal to a sample plate (not shown in FIG. 1A), which is to be inserted and secured in this recess. In its peripheral portion, the carrier body 22 supports a mechanical locking mechanism 26 for reliably locking a sample in the carrier body 22 and a resettable memory device 28, e.g., an electronic device, such as a integrated circuit (IC) chip for storing information removably inserted into a recess 30 formed in the carrier body 22.

Furthermore, in its peripheral portion, the carrier body 22 has through holes 32, 34, and 36 for engaging with a T-shaped mechanical actuator of the mass spectrometer loading system of the type disclosed in our co-pending U.S. patent application Ser. No. 10/615,733.

Figure 1B:
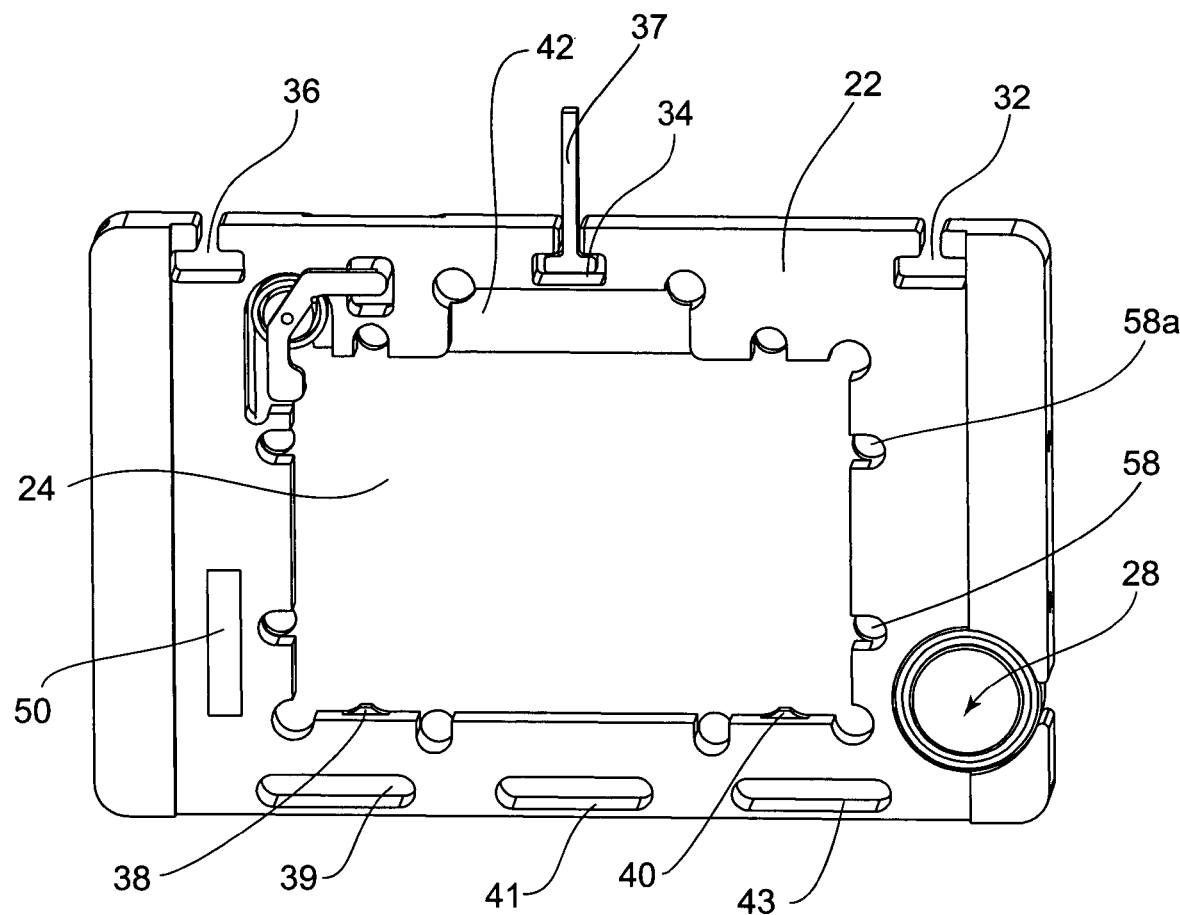
FIG. 1B is a view of the sample plate carrier of FIG. 1A with the T-shaped projection of the gripping mechanism inserted into the complementary T-shaped slot of the sample plate carrier.

It is recognized that the sample plate carrier can have mechanical features to accommodate different types of robotic grips. This is beneficial since the sample plate carrier can travel between different robotic systems during sample preparation and sample analysis. FIG. 1B is a view of the sample plate carrier of FIG. 1A with the T-shaped projection 37 of the gripping mechanism inserted into the complementary T-shaped slot 34 of the sample plate carrier 20. Alternatively, openings 39, 41, 43 shown and designated in FIGS. 1A and 1B can be used for engagement with claw-like mechanical of electromechanical actuators (not shown). There are also openings for interaction with a receiver/inserter described later.

The recess walls have small projections 38 and 40 (FIG. 1B) and a recess 42 with a flat bottom machined into the carrier body 22 to insure that the front side of the sample plate, not shown in FIG. 1A and defined as the side with samples, is spaced apart from the carrier body 22 to protect the samples from mechanical damage and contamination. The aforementioned recess 42 is needed to accommodate a conforming projection with a positioning hole on a standard sample holder described in the aforementioned patent application.

The sample plate carrier body 22 can be made from various materials, e.g., a plastic materials, preferably with charge dissipating properties to prevent dust accumulation.

In the preferred embodiment, the electronic device 28 (hereinafter referred to as nonvolatile information storage device) is the DS 1996L device with 64 K NV RAM commercially produced by Dallas Semiconductor. It is understood that the aforementioned IC chip is given only as an example and that a great variety of similar devices may be used. The DS 1996L is a nonvolatile recordable electronic memory device in a stainless steal capsule that has a convenient well-defined read-write protocol.

The information from this device can be scanned out by establishing only two data input/output electrical connections with two opposite halves of the capsule called the ground and the data. Also only two data input/output electrical connections are needed to write information into DS 1996L device. For the operation with a high throughput system the nonvolatile information storage device 28 can be preprogrammed by the user to record in its memory the sample info and the sample history as well as to have either direct instruction set or methods for the mass spectrometer or to have a pointer to a method file located either on a mass spectrometer computer or on other computers accessible by the mass spectrometer computer network. This information may contain an index reference to a particular sample plate currently held by the carrier. Such index reference may comprise a barcode or a number engraved directly on the sample plate for tracing the path of the sample plates through the system. It is possible that a part of the information on the device 28 can be prepared and recorded on an automated apparatus such as a sample deposition device, which is beyond the scope of the present invention, without direct human interference.

Alternatively or in parallel with the nonvolatile information storage device 28, it is also possible to use barcode technology by attaching a removable barcode sticker. As can be seen from FIG. 2, which is a three-dimensional view of the sample plate carrier 20 from the backside of the carrier, bar code stickers 44, 46, 48 can be attached to the flat backside of the carrier body 22.

It may also be desirable to have a permanent factory-unique bar code on the sample holder 20 that can be positioned, for example, on the front side of the carrier body 22 in such areas as the areas 50 shown in FIGS. 1A and 1B. It can be beneficial to have semi-permanent bar code sticker that identifies information on a specific research group or a sample group or a specific project. All this information can also be recorded within the nonvolatile information storage device 28.

Figure 2:
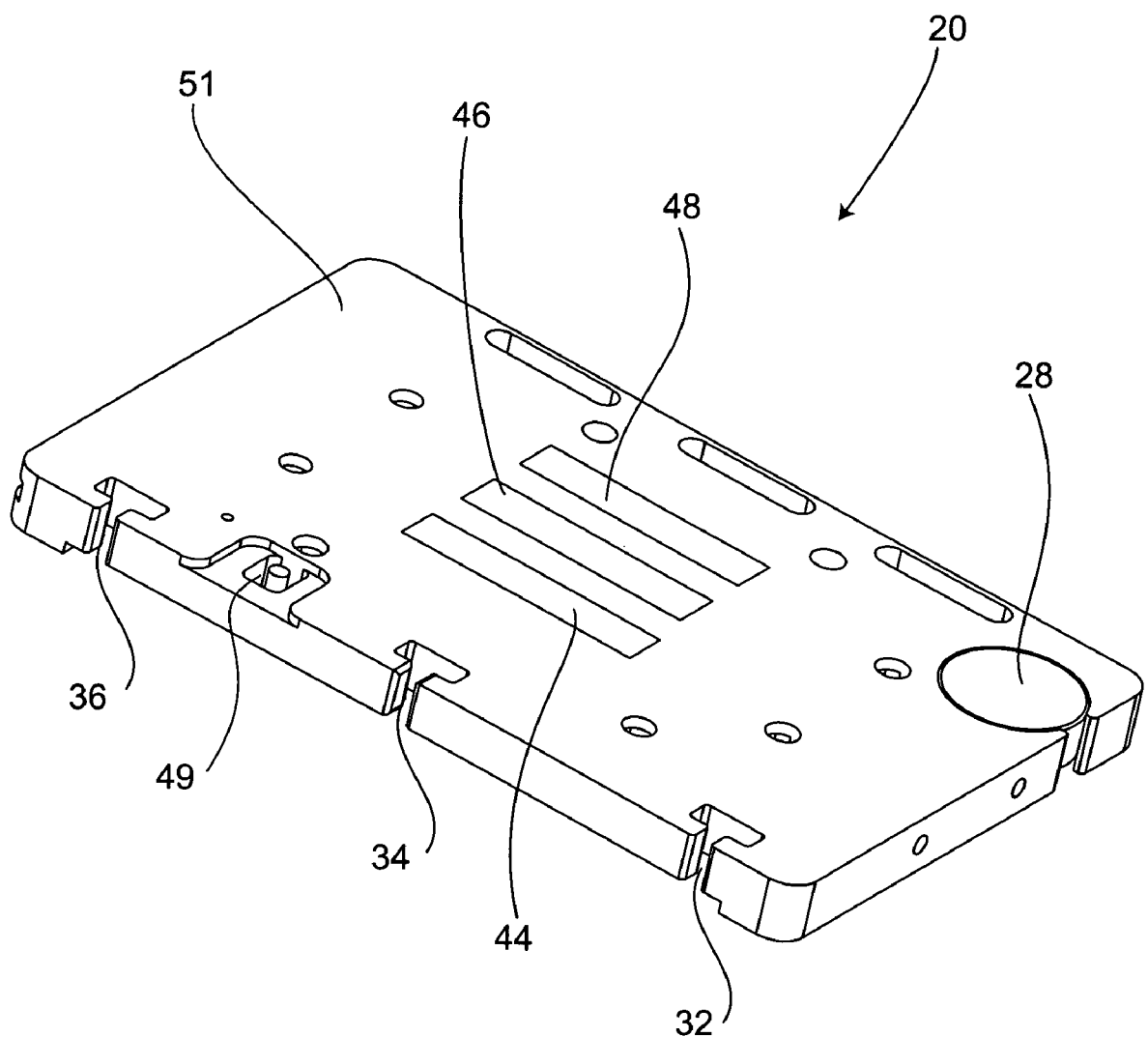
FIG. 2 is a three-dimensional view of the sample plate carrier from the backside of the carrier illustrating possible positions for location of bar codes.

The sample plate carrier 20 of the preferred embodiment of the present invention shown in FIGS. 1 and 2 is designed not only to carry the information on the sample plate but also to simplify sample plate handling by a mass spectrometer autoloading apparatus, e.g., of the type shown and described in our aforementioned pending patent application.

Figure 3:
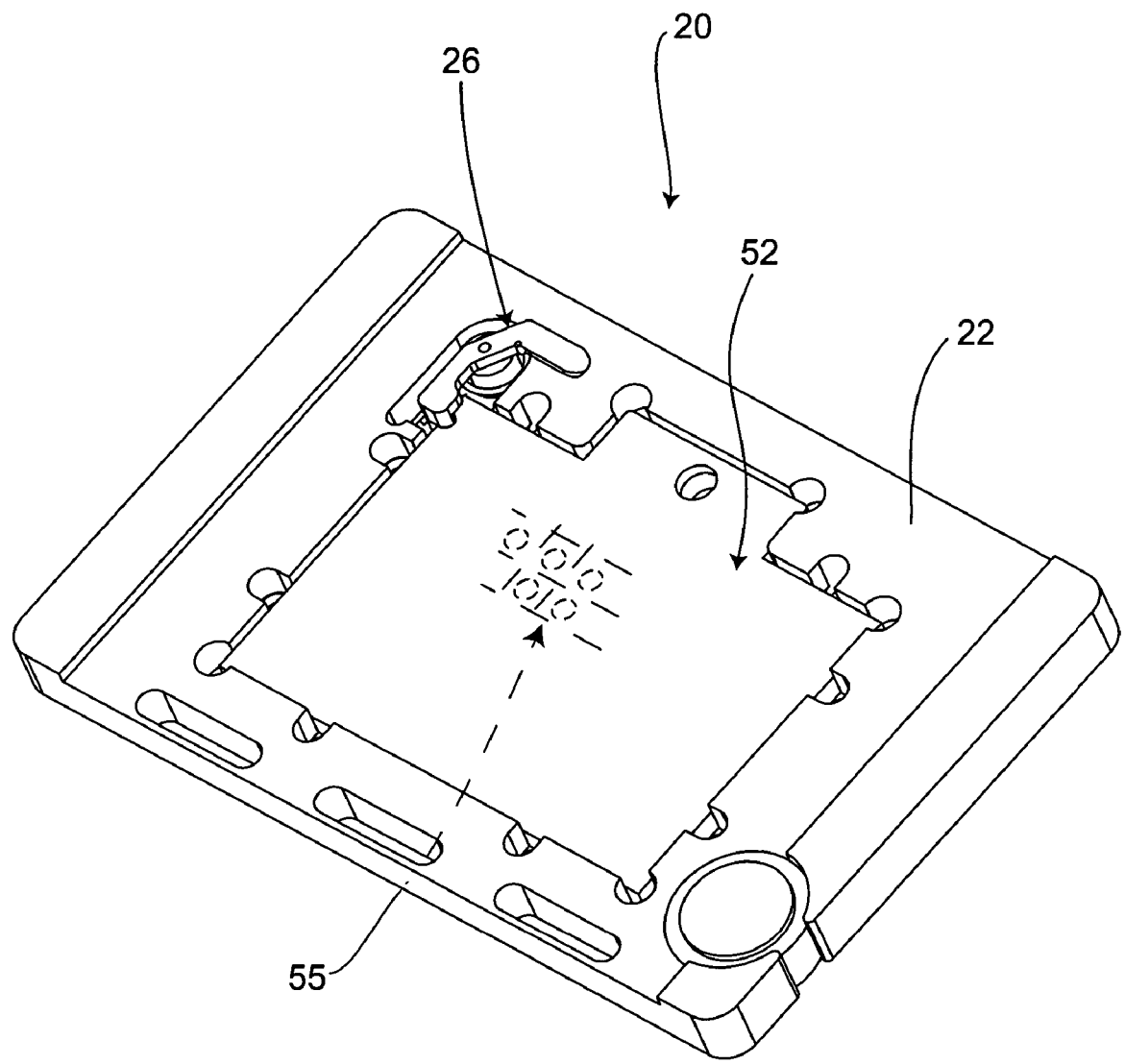
FIG. 3 is a three-dimensional view of the sample plate carrier of FIGS. 1 and 1B with a sample carrier installed into the carrier body and clamped by the locking mechanism of the preferred embodiment of the present invention.

FIG. 3 is a three-dimensional view of the sample plate carrier 20 of FIG. 1A with a sample plate that shows a sample plate 52 installed into the carrier body 22 and secured by the locking mechanism 26. Reference numeral 55 designates samples which are located on the invisible front side of the sample plate 52.

Figure 4:
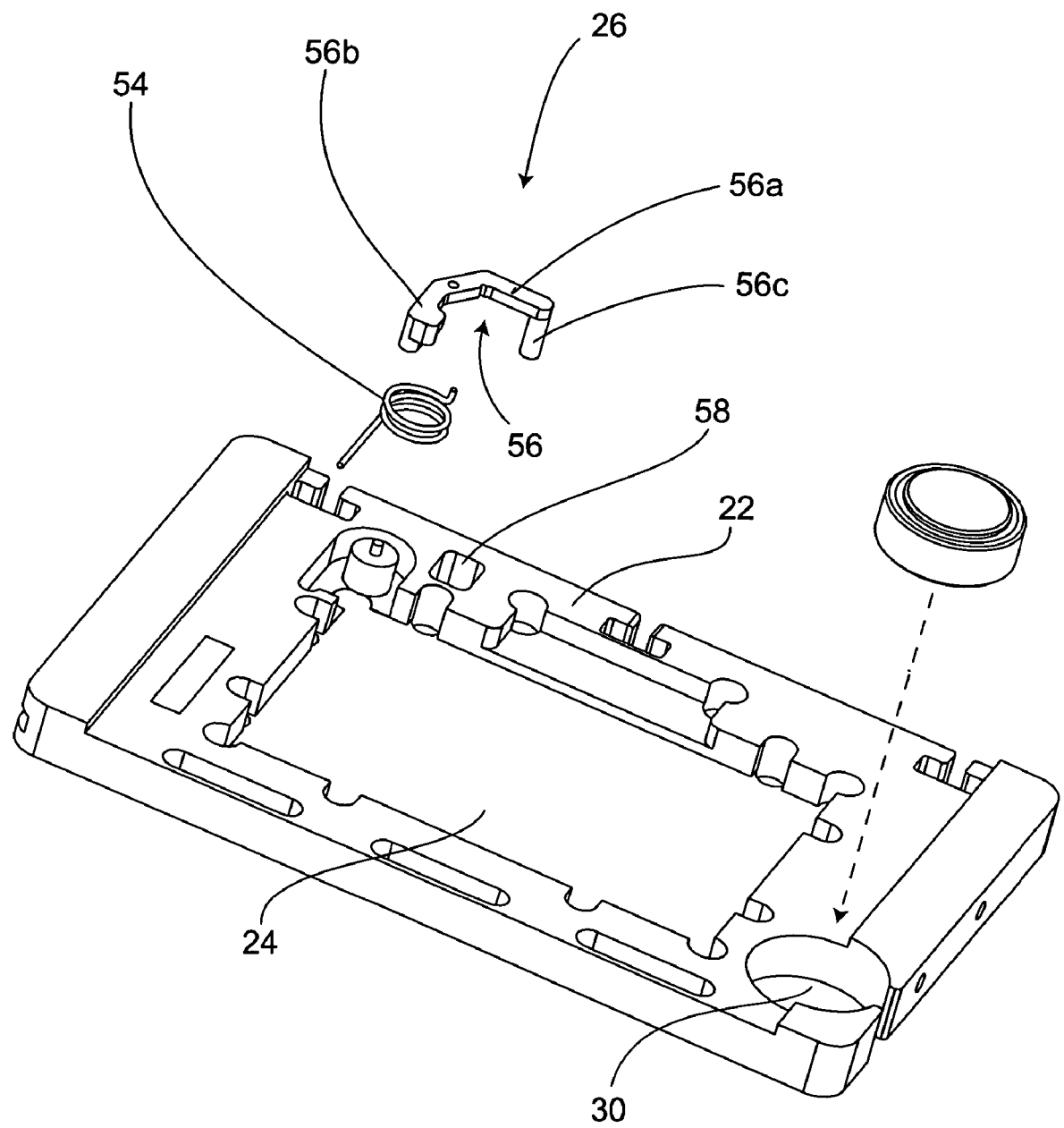
FIG. 4 is an exploded three-dimensional view of the sample plate carrier illustrating the details of the locking mechanism.

FIG. 4 shows an exploded view of the locking mechanism 26. It can be seen that this mechanism consists of a spring 54 and a locking element 56. The locking element has a form of a two-arm lever with arms 56a and 56b. The arm 56a has, on its end, facing the carrier body 22, a projection 56c for engagement with a recess 58 in the carrier body 22. Normally, the spring 54 presses the arm 56b against the sample plate 52 inserted into the recess 24 of the carrier body 22. By pushing on the arm 56a against the force of the spring 54, the arm 56b unlocks the sample plate so that it can be replaced.

Mechanical actuators or grippers of the type disclosed in our aforementioned pending Patent Application handle the sample plate carrier 20 of the present invention together with the sample plate 52 as a single part. If necessary, the sample plate 52 can be separated from the sample plate carrier 20, e.g., by the gripper or actuator of a specific design. This may be required, e.g., for automatic insertion of the sample plates prepared for analysis into the carrier body 22.

Figure 5:
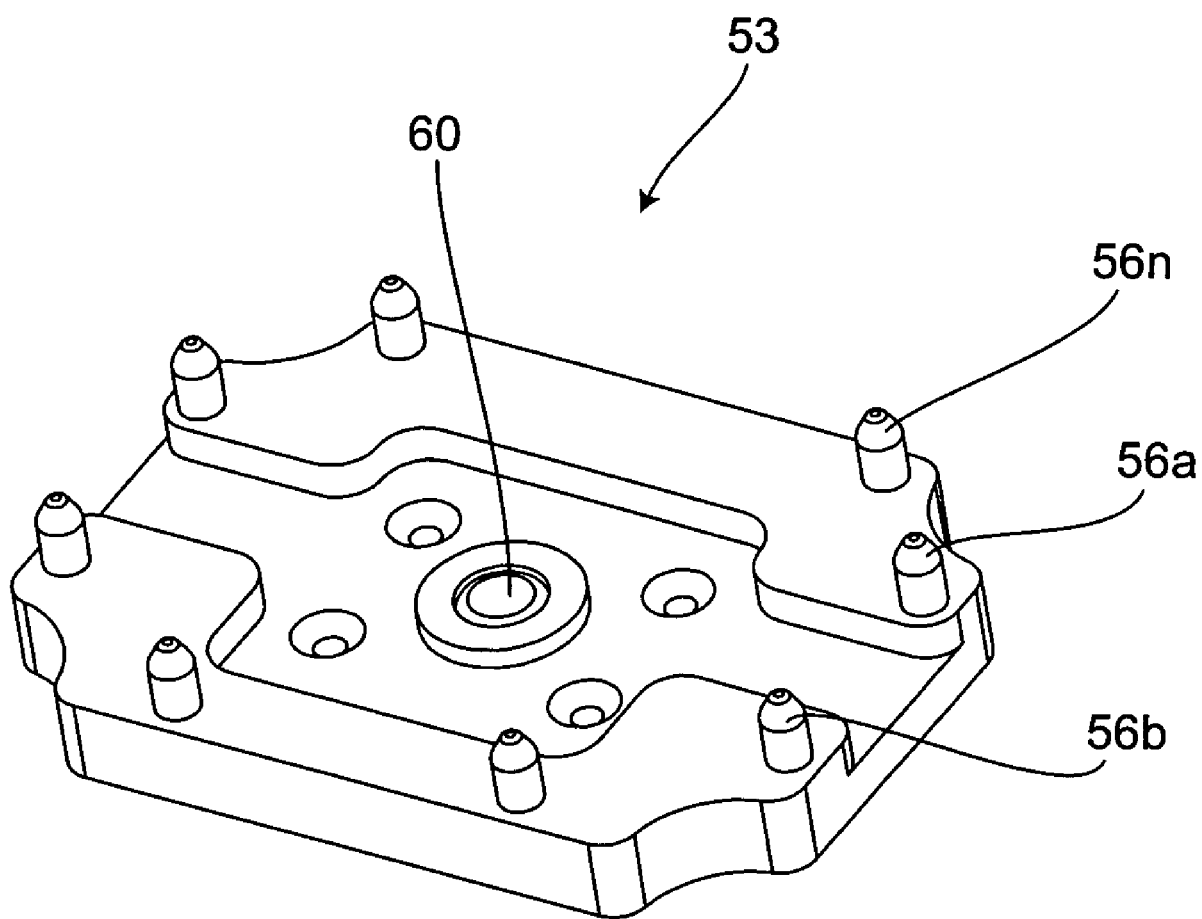
FIG. 5 is a three-dimensional view of a sample-plate receiver/inserter suitable for automatic removal of the sample plates from the sample plate carrier body and for automatic insertion into the sample plate carrier body.

FIG. 5 is a three-dimensional view of a sample-plate receiver/inserter 53 (hereinafter referred to as the receiver 53) suitable for automatic removal of the sample plates 52 from the sample plate carrier body 22 or for automatic insertion into the sample plate carrier body 22. The receiver 53 has locating pins 56a, 56b, . . . 56n arranged on the receiver's periphery. These pins are intended for aligning the position of the receiver relative to the sample plate 52 due to engagement with the positioning holes 58a, 58b, . . . 58n formed in the carrier body 22 over the periphery of the recess 24 (FIG. 1A). What is meant in this context under the term periphery or peripheral portion is an area outside the recess. The center of the receiver 53 has a magnet 60 used to attach the sample plate 52 to the receiver 53 if the mechanical lock 26 is open.

Figure 6:
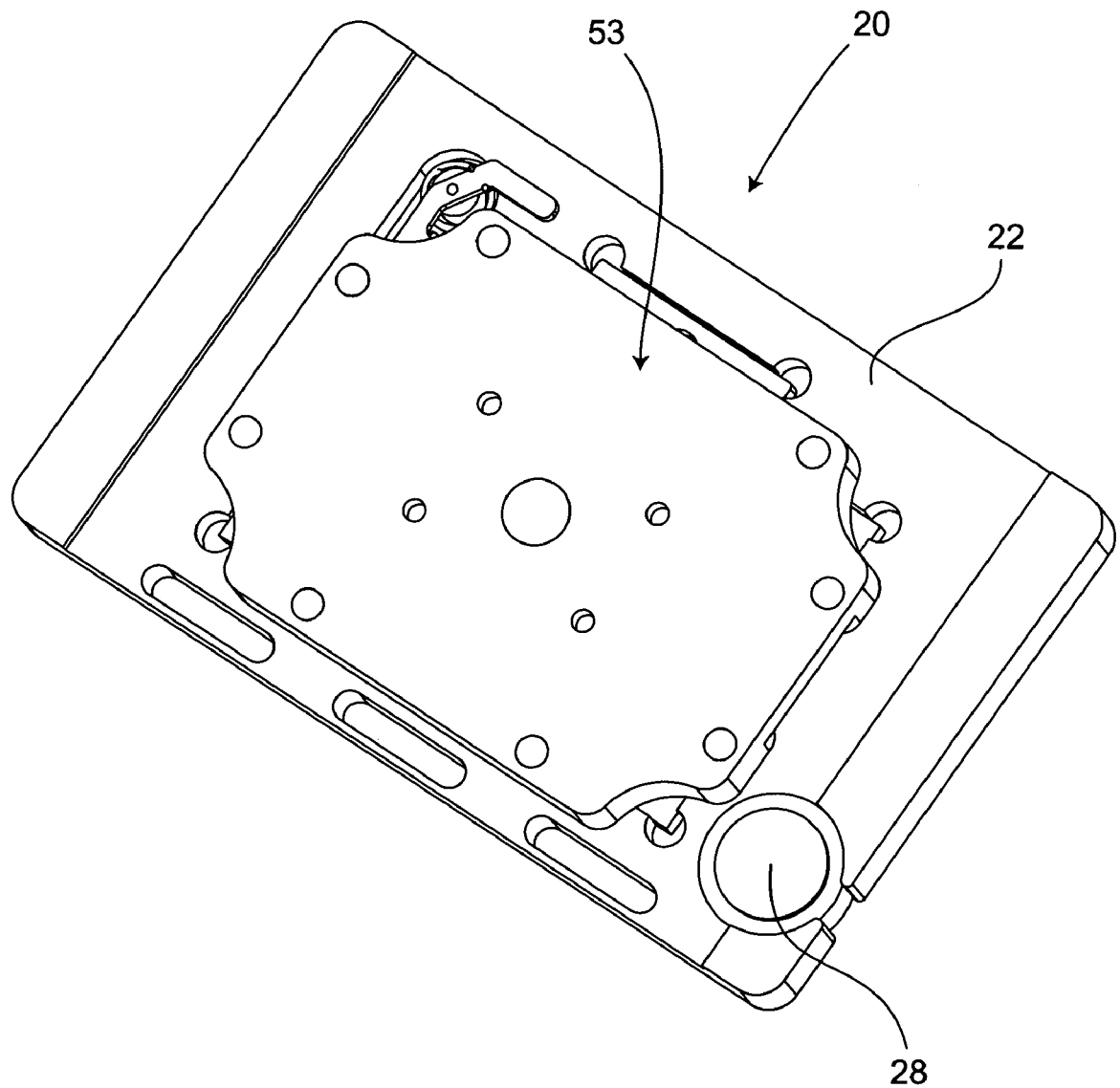
FIG. 6 is a three-dimensional view illustrating the aligned position of the receiver on the sample plate carrier body for extracting the sample plate.

FIG. 6 is a three dimensional view illustrating the aligned position of the receiver 53 on the sample plate carrier body 22 for extracting the sample plate. To transfer the sample plate 52 to the receiver 53, it is sufficient to open the mechanical locking device 26 (if necessary, this can be done automatically with a special mechanism) and to grab the magnetic sample plate 52 directly from the carrier body 22, minimizing manual operations associated with insertion or removal of the sample plates from respective carriers.

Figure 7:
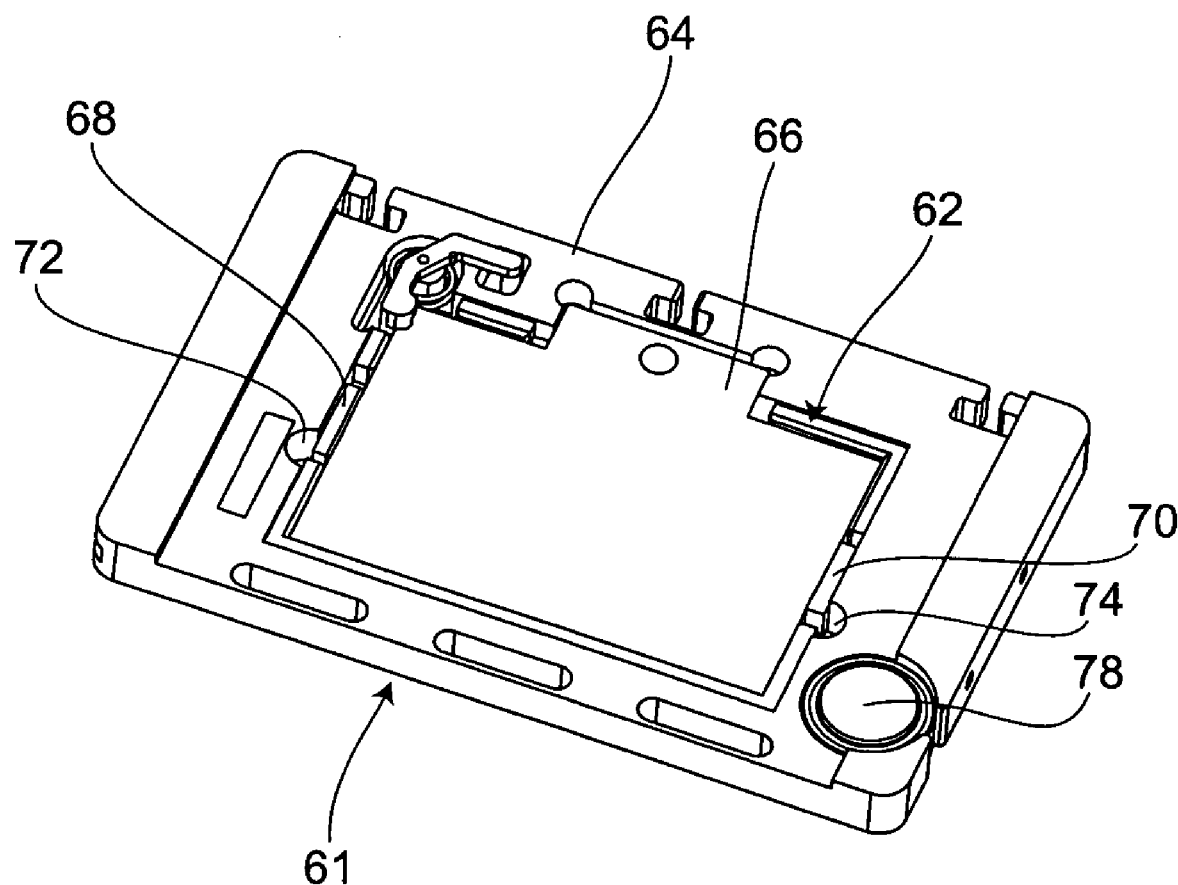
FIG. 7 is a three-dimensional view of a sample plate carrier of the second embodiment of the invention with an additional removable protective shield, which is installed into the sample plate carrier body.
Figure 8:
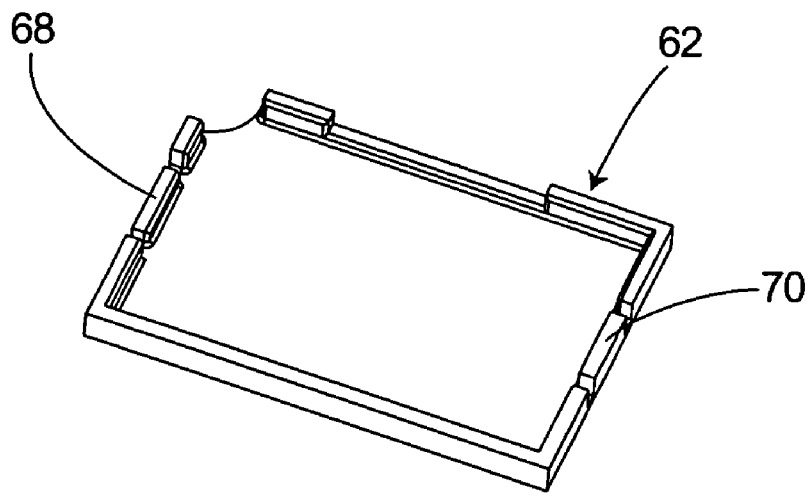
FIG. 8 is a three-dimensional view of the removable protective shield.
Figure 9:
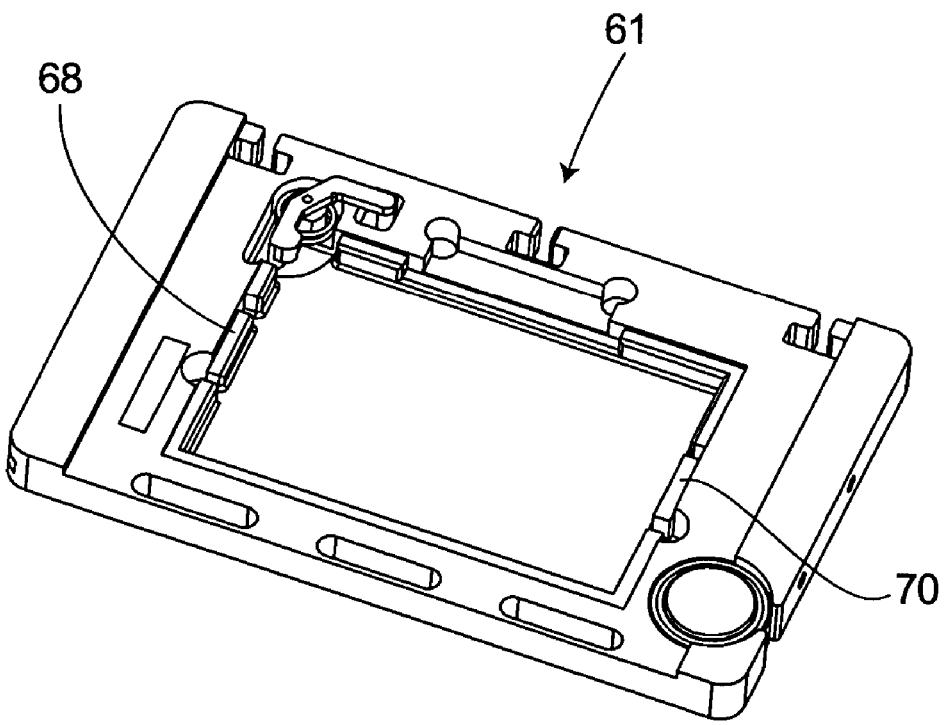
FIG. 9 is a view of the sample plate carrier body with the shield inserted but with the sample plate removed.

FIG. 7 is a three-dimensional view of a sample plate carrier 61 of the second embodiment of the invention with an additional removable protective shield 62, which is installed into the sample plate carrier body 64 between the sample plate 66 and the carrier body 64. This protective shield is used for covering the bottom of the recess 24 (FIG. 1a) and thus protecting the samples from possible contamination that otherwise could be accumulated in the recess. Prior to insertion of a new sample plate into the same sample carrier, the protective shield 62 is removed and is replaced by a new clean shield. The protective shield can be made, e.g., from a transparent or semitransparent plastic film. FIG. 8 is a three-dimensional view of the removable protective shield 62, and FIG. 9 is a view of the sample plate carrier 61 with the shield 62 inserted but with the sample plate 66 removed. The removable protective shield 62 can serve as a disposable or washable element that is changed each time when the new sample plate is installed into the sample plate carrier 61, thus additionally minimizing contamination issues.

The removable protective shield 62 of the second embodiment shown in FIGS. 7–9 has flexible tabs 68 and 70 to provide mechanical fixation for the shield 64 within the carrier body 64. The carrier body 64 of the sample plate carrier 61 of the second embodiment has holes 72 and 74 machined in the direct proximity with the position of the locking tabs 68 and 70 to simplify removal of the shield 62 from the carrier body 64.

For example, the protective shield 62 can be removed by pushing the tabs 68 and 70 out from the sample plate carrier 20 either manually or with tweezers. Similar to the first embodiment, the sample plate carrier 61 of the second embodiment has a nonvolatile information storage device 76 and a mechanical locking mechanism 78 to hold the sample plate 66 within the carrier body 64.

The following is the description of the second part of the system of the invention, i.e., of the information input/output station, which will be exemplified as a storage cassette for the sample plate carriers described above.

Figure 10:
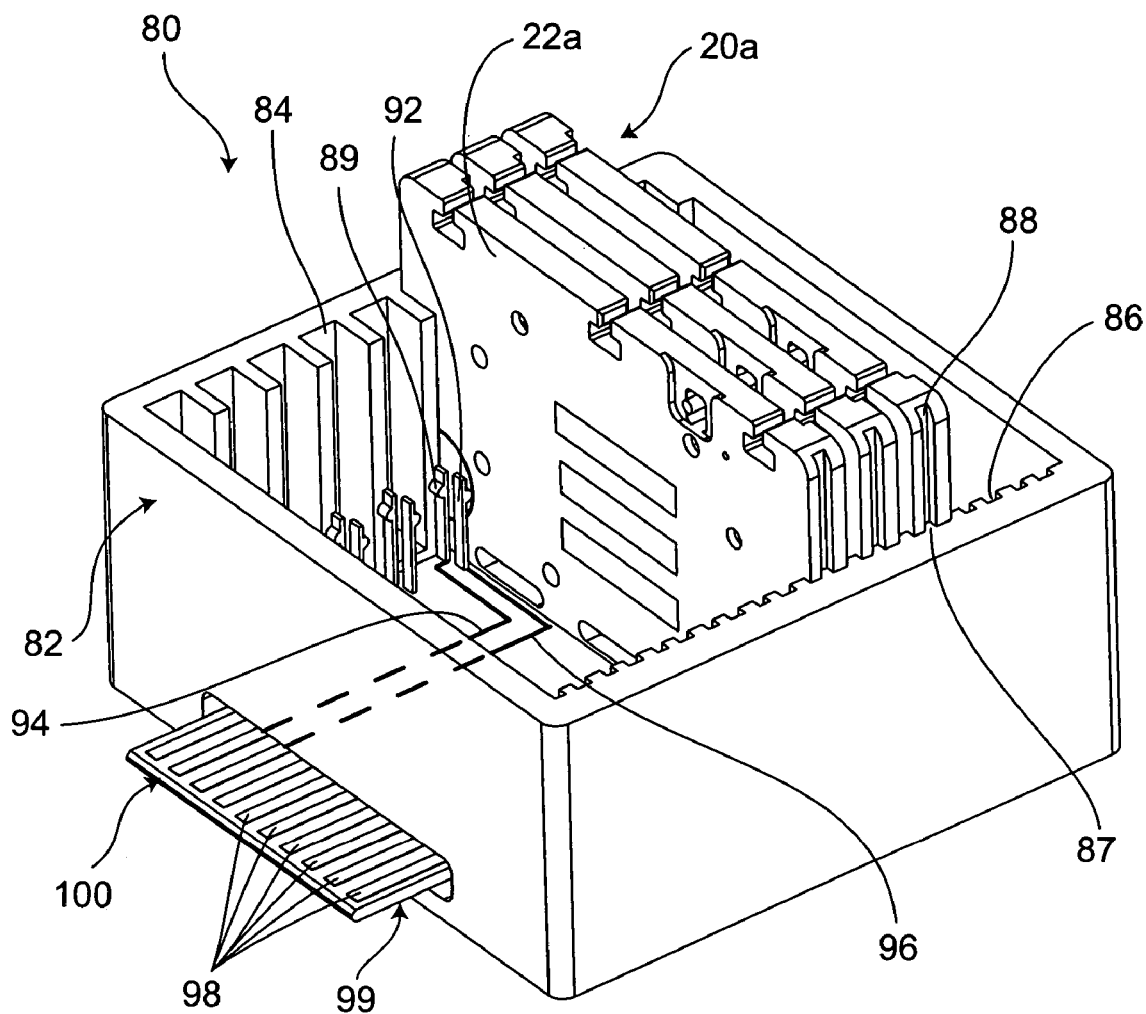
FIG. 10 is a three-dimensional view of a storage cassette for holding a plurality of sample plate carriers of the invention.

FIG. 10 is a three-dimensional view of a storage cassette for holding a plurality of the aforementioned sample plate carriers 20 (or 61) of the invention. As can be seen from FIG. 10, the cassette 80 comprises a box-like casing 82 with slots 84 on one inner side wall of the casing 82 and with slots 86 on the opposite inner side wall of the casing 82. As has been mentioned earlier, the sample plate carrier 20 of FIGS. 1A and 1B (or the sample plate carrier 61 of FIG. 7) may have a non-symmetrical mechanical features that can be advantageously used for unique orientation of sample plate carriers 20a within storage or operational cassettes or autoloading apparatuses. For example, the slots 84 on one side of the cassette may be wider than the slots 86 on the other side and have a width corresponding to the total thickness of the carrier body 22a. On the other hand, the slots 86 may have a narrower width to form projections 87 between the adjacent slots for insertion into the respective groove 88 on the side surface of the sample plate carrier 20a. In this case, it is possible to insert sample plate carrier into the cassette in only one specific orientation. It should be noted that all electrical contacts, lead wires, and the output terminals 98 of the port 100 can be formed on a printed circuit board 99.

As has been mentioned above, nonvolatile information storage device 28 may comprise a commercially produced electronic unit, e.g., the one manufactured by Dallas Semiconductor. The cassette 80 is provided with electrical contacts for individual and selective electrical connection to the input/output terminals of the nonvolatile information storage device 28 of each sample plate carrier loaded into the cassette 80. This features allow for inputting/outputting data into/from the storage devices 28 of sample holders selected by the central processing unit of the mechanism for handling the carriers with the samples, while these carriers are located in the cells of the cassette 80. In other words, the cassette 80 may be used as a unit for loading/unloading information.

Figure 11:
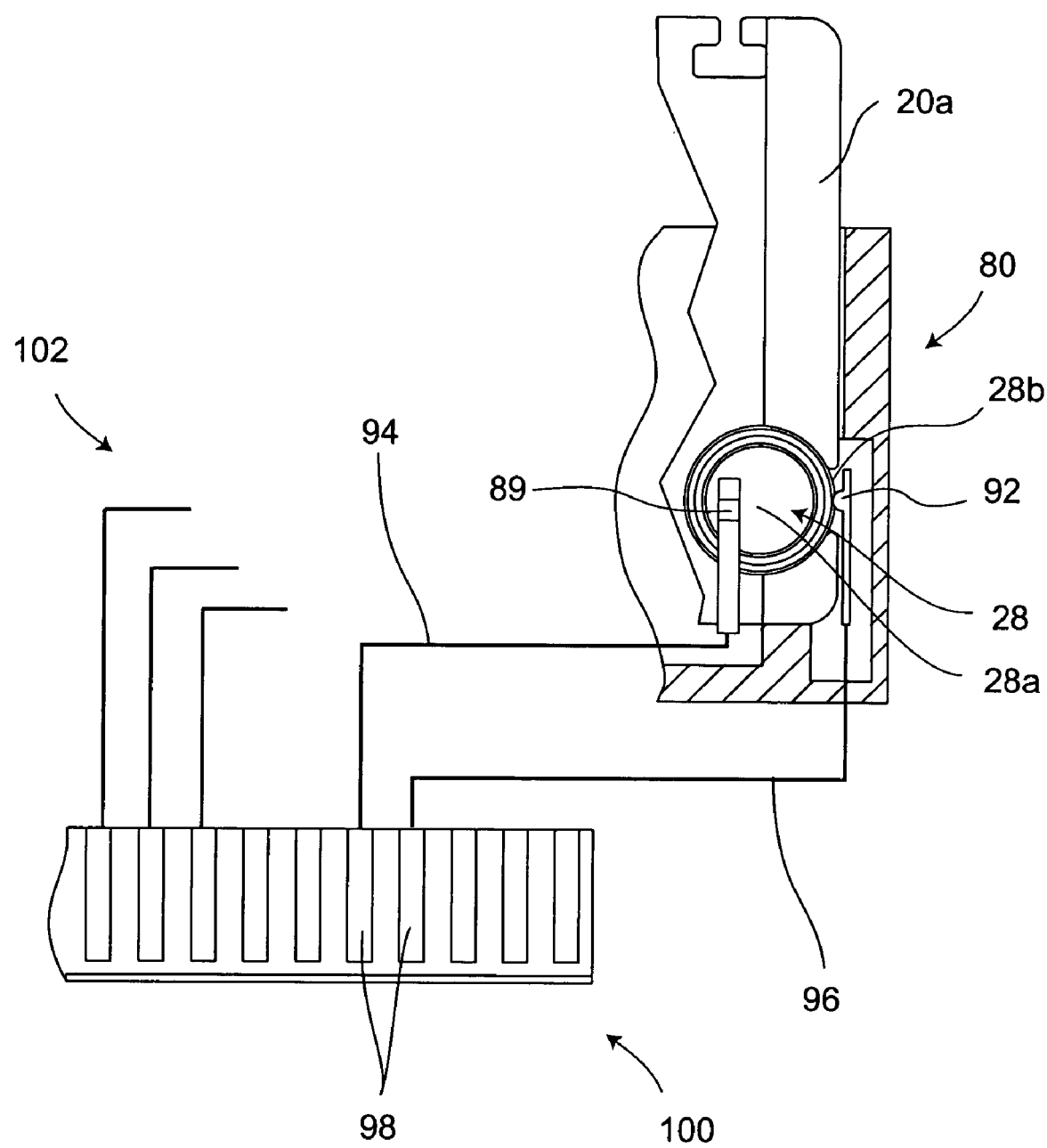
FIG. 11 is a schematic view of electrical connection between contacts of the storage cassette and the terminals of the memory device in the sample plate carrier.

An example of such a system with reference to the specific example of the aforementioned nonvolatile information storage device 28 (FIG. 1A) produced by Dallas Semiconductor will now be shown and described with reference to FIGS. 10 and 11, wherein FIG. 11 is a simplified electric diagram illustrating electrical connections of the information storage device 28 with contacts of the sample plate carrier cassette 80. In this drawing, the sample plate carrier 20a is shown by imaginary lines in order not to obscure the view of the contact elements. More specifically, the information storage element 28 has a shape of a button with one flat side of the button being a signal contact 28a and the cylindrical sidewall being an earth contact 28b (FIG. 11). Correspondingly, each slots 84 of the cassette (FIG. 10) has a metal strip or a metallized portion 90 on the side surface of the slot 84, which faces the contact surface 28a of the button-shaped element 28 and has an electric contact therewith when the holder is inserted into the slot 84. On the other hand, the surface of the slot 84, which faces the cylindrical surface of the element 28 has a spring-loaded contact 92 for engagement with the earth contact 28b of the respective element 28. In the embodiment of FIG. 10, the aforementioned metal strip 90 is replaced by a spring-loaded contact 89 similar to the contact 92.

As shown in FIG. 11, the lead wires 94 and 96 are formed on the printed circuit board 99 and connected to the output terminals 98 of the port 100. It is understood that such connections between the contacts of the cassette slots and the output terminals, as shown for the contact elements of the slot 84, exist for all other guide slots of the cassette. This is shown conventionally by lead wires 102 (FIG. 11). The port 100 of the cassette 80 can be connected to an appropriate central processing unit of the entire system or to separate systems automatically, e.g., with installation of the cassette to a working position.

Figure 12:
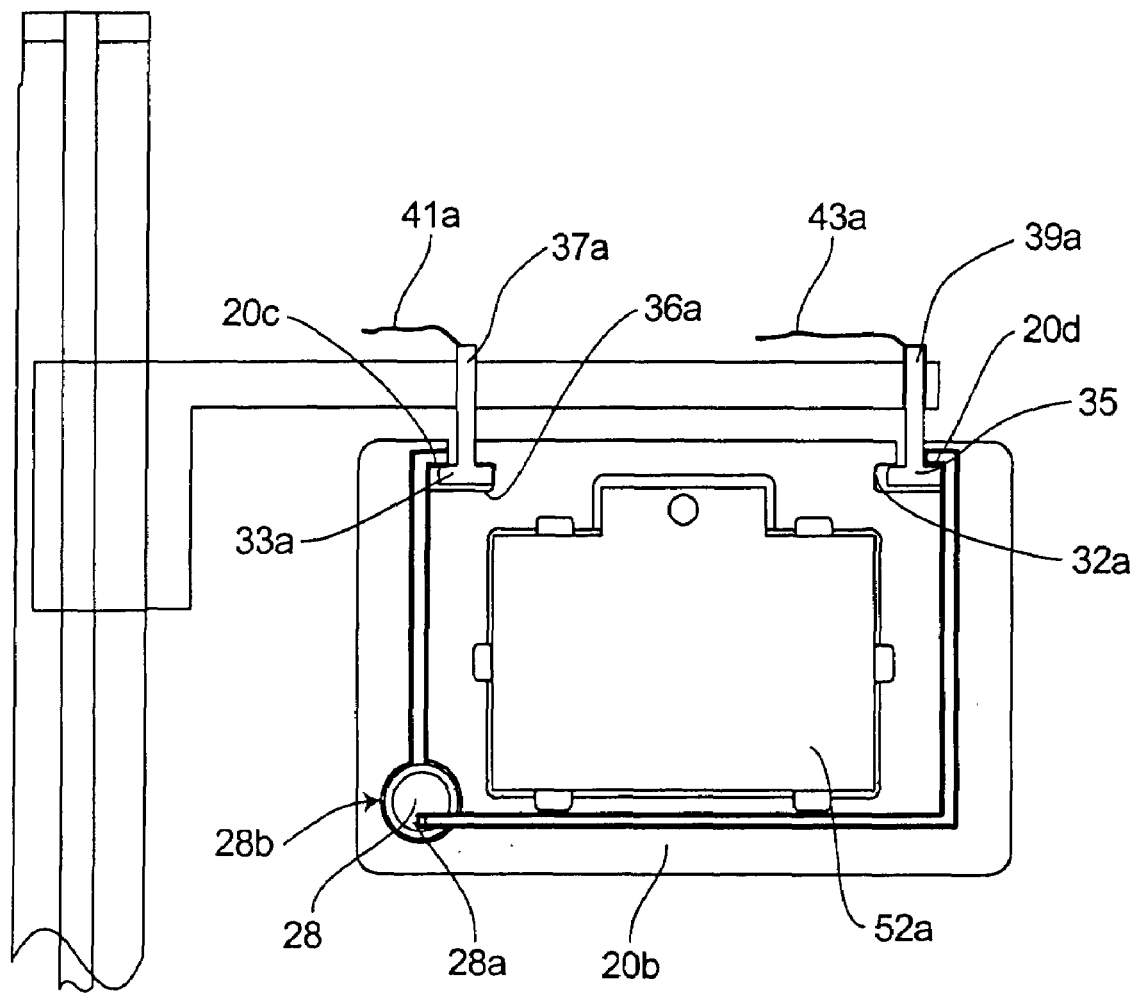
FIG. 12 is a view on the sample plate carrier in accordance with another embodiment for inputting/outputting data through contacts of the sample plate carrier memory device with contacts of the T-shaped grippers.

FIG. 12 is a view on the sample plate carrier 20b in accordance with another embodiment of the invention. In this embodiment, the first pair of input/output contacts 28a and 28b of the sample plate carrier 20b for inputting/outputting data has input/output terminals 20c and 20d, respectively, in the T-shaped slots 32a and 36a of the sample plate carrier 20b. On the other hand, the second pair of the input/output contacts 33a and 35a is built into respective T-shaped projections 37a and 39a. The contacts 33a and 35a are connected by conductors 41a and 43a, e.g., to a central processing unit (not shown) or to a similar data acquisition and processing device. In the system of this embodiment, inputting/outputting of the information into and from the memory element 28c is carried out during handling of the sample plate carrier 20b with the respective sample plate 52a via electrical connection between the contacts of the sample plate carrier with the contacts of the T-shaped projections of the gripper.

Figure 13:
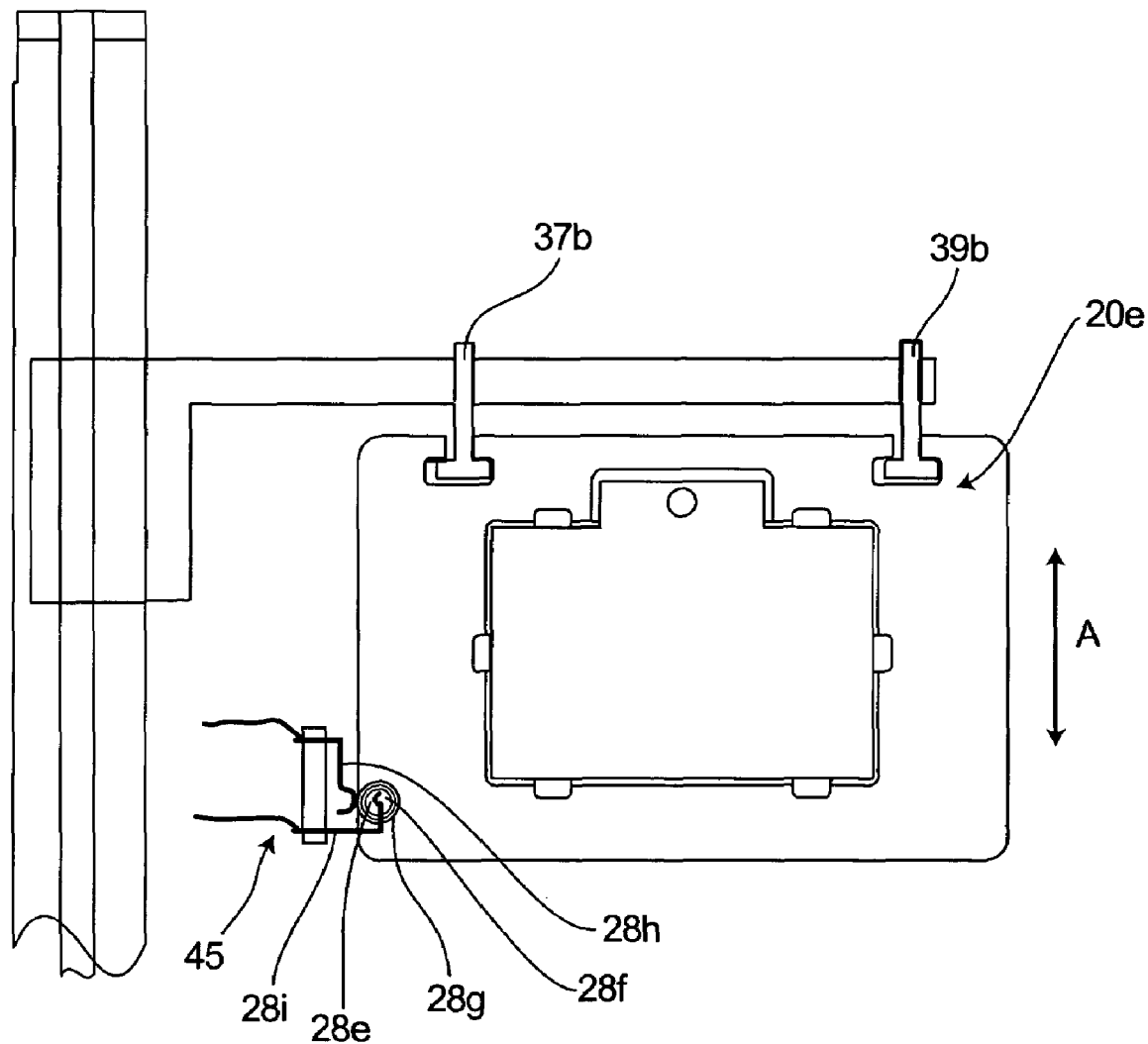
FIG. 13 is a view of sample plate carrier in accordance with still another embodiment for inputting/outputting data through contacts of the sample plate carrier memory device with contacts of an intermediate station.

FIG. 13 is a view of sample plate carrier 20e in accordance with still another embodiment for inputting/outputting data through contacts of the sample plate carrier memory device 28e with contacts of an intermediate station 45. The intermediate station 45 has a second pair of contacts 28h and 28i for electrical interaction with respective contacts 28g and 28f of the memory element 28e. In this embodiment, inputting/outputting of data occurs when the sample plate carrier 20e supported by the T-shaped grippers 37b and 39b is passed in the direction of the arrow A through the intermediate station 45 for interaction of the first pair of contacts with the second pair of contacts.

Figure 14:
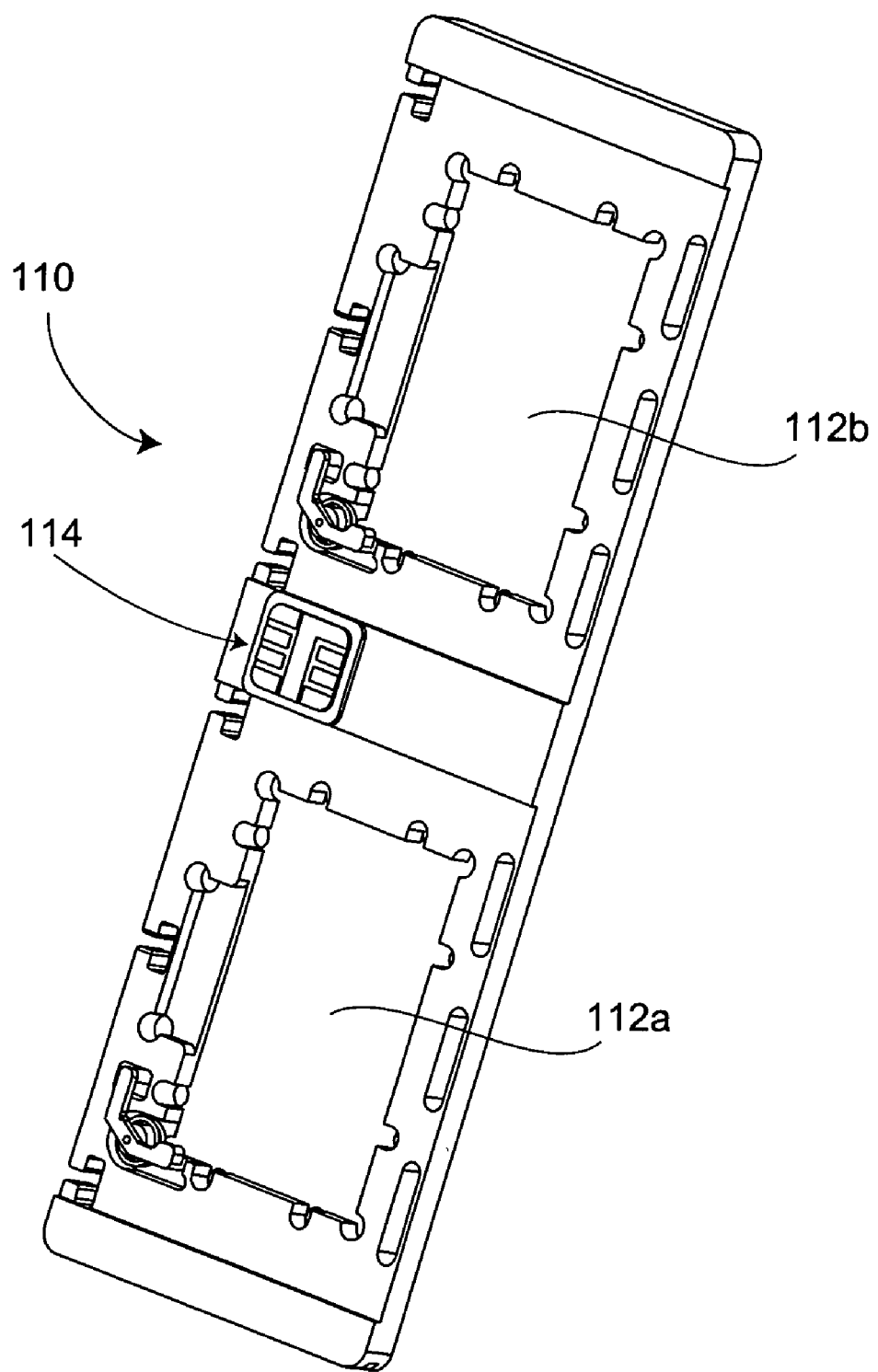
FIG. 14 is a three-dimensional view of a multiposition sample carrier of the invention.

FIG. 14 is a three-dimensional view of a multiposition sample plate carrier 110 of the invention. For the simplicity of the drawing and explanation, the sample plate carrier is shown only with positions for two samples plate 112a and 112b. The sample plate carrier 110 has a memory device 114 common for both sample plate locations 112a and 112b. In this embodiment, the memory device 114 is shown as an electronic smart chip device. The memory device 114 may be a commercially available "smart chip" device that is commonly used in banking cards, telephone cards, and the like. Smart chips are secure, compact and intelligent data carriers. The sample plate carrier 110 possesses versatility in that it can be used with two sample plates having identical samples, two sample plates with different samples, or with a single sample plate. One location, e.g., 112a, can be used for initial loading of the sample plate while the second location 112b, can be used for storing the plate with samples that have been previously processed or analyzed. Alternatively, one of the plates may carry control or reference samples and the other may carry the sample to be analyzed.

Figure 15:
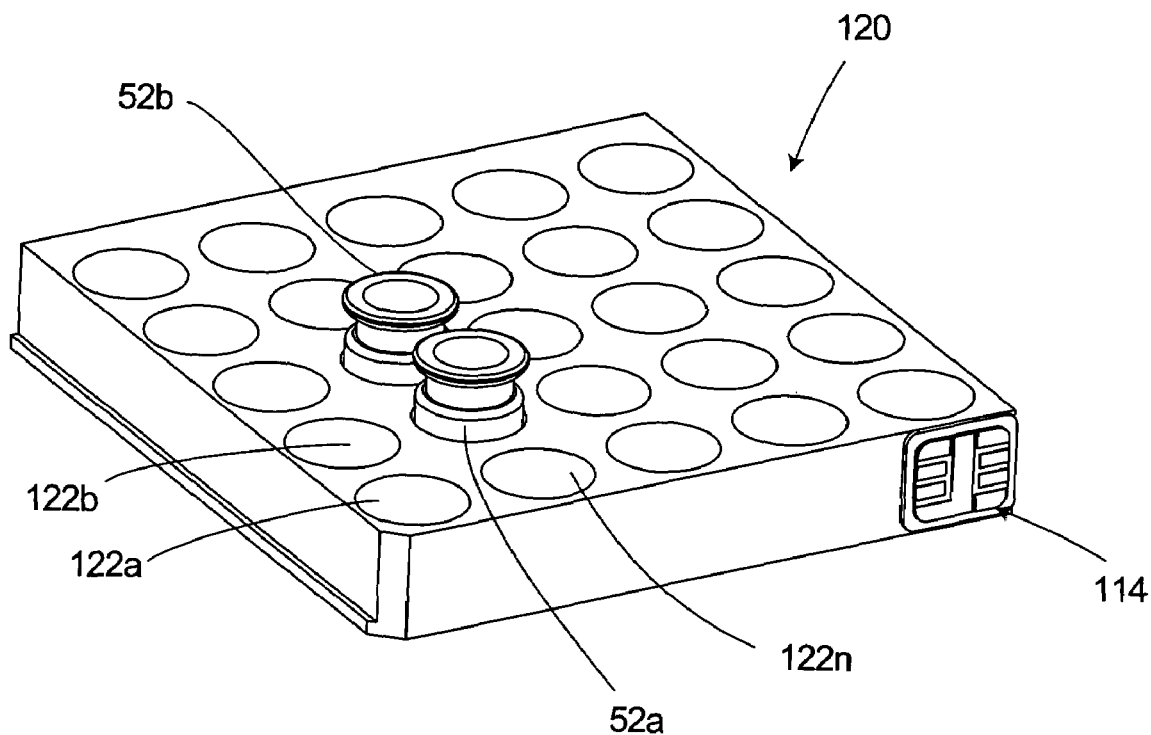
FIG. 15 is a three-dimensional view of a multiple-position sample vial carrier in accordance with an embodiment of the present invention for analysis and processing of liquid samples.
Figure 16:
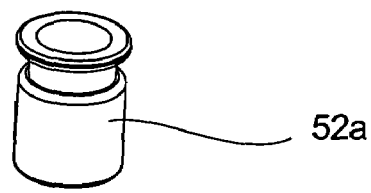
FIG. 16 is a three-dimensional view illustrating an example of a vial for liquid samples.

FIG. 15 is a three-dimensional view of a multiple-position sample vial carrier in accordance with an embodiment of the present invention for analysis and processing of liquid samples. FIG. 16 is a three-dimensional view illustrating an example of a vial for liquid samples.

In the embodiment of FIGS. 15 and 16, the sample vial carrier 120 comprises a multiple position plate with a plurality of recesses 122a, 122b, . . . 122n for insertion of small vials 52a, 52b, . . . filled with a liquid sample such as an aqueous solution of proteins or peptides intended for analysis.

An electronic memory device 114, e.g., of the same type as shown in the device of FIG. 14, can be attached to the side surface of the carrier 120.

The system shown in FIGS. 15 and 16 may constitute a part of a commercially used autosamplers for high performance liquid chromatography (HPLC) utilizing standard vials of the type shown in FIG. 16. An example of such commercial autosampler is the one offered by Agilent 1100 Series (Agilent Technologies Co., CA, USA) for a variety of tasks, ranging from general HPLC needs up to dedicated solutions for high sample throughput. The aforementioned system is equipped with a finger gripper for handling the vials. The same or a similar device can be used for sample analysis with capillary electrophoresis or gas chromatography. The final detector for analysis may comprise, e.g., a mass spectrometer, optical spectrograph, flame ionization device, etc.

In the embodiment of FIGS. 15 and 16, the vials 52a, 52b, . . . can be inserted into the respective recesses with a loose fit so that they could be easily inserted into the recesses manually or mechanically. For simplification of operational procedures it is recommended to record in the memory device 114 information only about the processing stages and events scheduled for the samples, without extraneous information about sample history, content, etc. In this case, each time when a new sample vial carrier is used, it will be prompted to the operator to input only the sample ID information.

The invention also provides a method for selective input and output of information into and from the memory element built into each sample plate carrier of a plurality of sample plate carriers that carry sample plates with samples for analysis. The method comprises the steps of:

providing a plurality of sample plate carriers, each holding at least one sample plate with specific samples to be analyzed and having a built-in memory element for inputting/outputting related information, said built-in memory element having first input/output contacts for inputting/outputting said information;

providing handling means for handling said sample plate carriers having second inputting/outputting contacts connected to a central processing unit capable of storing and processing said information; and inputting/outputting said information into/from said built-in memory elements while handling said sample plate carriers with the use of said handling means.

The aforementioned handling means may comprise either grippers for loading/unloading and transporting the sample plate carriers and sample plates or a storage cassette for the sample plate carriers. The storage cassette has individual cells for the sample plate carriers. In the case of the cassette, handling operation that consists of inserting the sample plate carriers into the cells while the operation of inputting/outputting the information into/from said memory element of each of said sample plate carriers is carried out when said sample plate carriers are located in said cells of said storage cassette.

Thus, it has been shown that the present invention provides a sample plate carrier that incorporates a memory device, is suitable for high throughput analysis of high-volume samples, is suitable for genomic MALDI mass-spectrometric study, may carry a magnetic strip or barcode for information recording, may be compactly packed into cells of a sample storage cassette with means for individual access to the memory element of each sample plate carrier through the inlet port of the cassette, is universal in that it can interact with various gripping mechanisms for serving units of analytical equipment in the line of analysis, allows for replacement of the sample plates of different geometry with rewriting data in accordance with characteristics of new samples, is free of contamination during handling and does not require the use of removable stickers with information, provides unique correlations between information data, sample plate with a specific samples, and methods of analysis, has a reliable lock to prevent a sample plate from accidental disengagement from the carrier, and may have a non-symmetrical geometry to insure unique orientation of the holder in the cassette and other carrier holding devices.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, the sample plate carrier may have a simplified design for manual handling. FIG. 2 illustrates that the locking element 56 of the locking mechanism 26 in the preferred embodiment of the present invention is also accessible from the backside 51 (FIG. 2) of the carrier body 64 by protruding through the opening 49. In this case, the locking element 56 can be easily controlled by a human operator from both sides of the carrier body 64, so that the carrier body 64 can be used as a sample plate picking or grabbing device to pick sample plates manually (or by a robot) from a lab table or sample deposition workstation.

The sample plate carrier body can be designed to accommodate a variety of the geometrical shapes of the sample plates. If necessary, the carrier body may have several cavities to carry several sample plates on one sample holder. The carrier body may have the same outer dimensions and different inner cavities to accommodate variety of the sample plates within the same robotic or auto loading systems. The locking mechanisms may have various designs. For example, the flexible element and the locking element for the mechanical lock can be made out of the same plastic material as the carrier body and can be molded as one combined part. It is also possible to use locks and springs of other types than those shown in the drawings for holding the sample plate. The sample plate may be held by electromechanical means such as an electromagnet or by a permanent magnet. The samples may be of different types and not necessarily of a biological nature. The results of analysis on each spot of the sample plate can be as simple as being positive or negative, 0 or 1, "Yes" or "No", "Pass" or "Not pass", etc. Recording of that information on the sample plate carrier that may have a mechanical attachment to the sample plate has a benefit of streamlining the data flow process and insuring the accuracy for all records. It also provides an easy way to repeat the same or additional analysis if needed for conformation. Even though the mass spectroscopy can be more sensitive to contamination and can require higher degree of the sample protection compared to other analytical techniques, it is recognized that both the sample plate carrier with a nonvolatile electronic memory and the method of operation of the present invention can be used not only to handle samples and information flow for mass spectroscopic applications, but also to handle other types of sample arrays for various analysis. For example, the sample holder of the present invention with an onboard electronic memory can be used to handle glass plates with deposited biological sample arrays for analyzing by optical spectroscopy techniques (including but not limiting to fluorescent UV-visible or infrared spectroscopy). The information can be inputted/outputted into/from the memory elements at a separate station away from the cassette and prior to their insertion into the sample plate carriers. The memory unit may be different from the aforementioned button-shaped device, and the sample plate carrier can be provided with a USB memory stick device, an electronic flash memory unit, electronic smart card, a miniaturized hard drive, etc.

The invention claimed is:

1. A system of sample plate carriers for handling with sample plate carrier handling means, said system comprising:
   a plurality of sample plate carriers, wherein each sample plate carrier of said plurality comprises:
   a carrier body having means for supporting at least one sample carrying plate with at least one sample;
   memory means built-in into said carrier body, said memory means having first memory input/output contacts for inputting/outputting information;
   engagement means provided on said carrier body for engagement with said sample plate carrier handling means; said engagement means having second inputting/outputting contacts;
   a central processing unit connected to said second input/output contacts and connectable to said first input/output contacts of said memory means when said engagement means engages said sample plate carrier handling means;
   a storage cassette that comprises a plurality of cells for insertion of said sample plate carriers, second input/output contacts being provided in each cell of said plurality of cells for electrical contact with said first input/output contacts of said carrier bodies when said carrier bodies are inserted into said cells;
   an inlet/outlet port on said storage cassette with a plurality of electrical terminals, each of said electrical terminals being electrically connected to respective second input/output contacts of a respective cell of said storage cassette
   wherein said sample plate carrier handling means comprises at least two different gripping mechanisms and wherein said engagement means of said carrier body comprises at least two sets of different openings for interaction with said at least two different gripping mechanisms.

2. The system of claim 1, wherein one set of said two sets of different openings are T-shaped openings and a plurality of openings arranged with a predetermined pattern, one of said two gripping mechanisms comprising a gripper having T-shaped projections insertable into said T-shaped openings and the other of said two gripping mechanisms is a sample-plate receiver/inserter having projections arranged with the same predetermined pattern as said plurality of openings and engageable with said plurality of openings for receiving/releasing said sample medium from sample medium carriers.

3. The system of claim 1, wherein said means for supporting said at least one sample-carrying plate with at least one sample is a recess formed in said carrier body, said system being further provided with a removable protective shield insertable into said recess of said carrier body as an additional means for protecting said samples and said sample-carrying plate from contamination.

4. The system of claim 1, further provided with a lock for locking said sample plate in said carrier body.

* * * * *